(12) United States Patent
Barrile-Josephson et al.

(10) Patent No.: US 7,780,689 B2
(45) Date of Patent: Aug. 24, 2010

(54) BAR-LINK DRIVE SYSTEM FOR A MICROKERATOME

(75) Inventors: Craig A. Barrile-Josephson, Rochester, NY (US); Michael H. Dobner, Honeoye Falls, NY (US); James Kirch, Scottsville, NY (US); Peter J. Halecki, Rochester, NY (US); Christopher Wagner, Rochester, NY (US)

(73) Assignee: Technolas Perfect Vision GmbH (DE)

( * ) Notice: Subject to any disclaimer, the term of this patent is extended or adjusted under 35 U.S.C. 154(b) by 1907 days.

(21) Appl. No.: 10/807,420

(22) Filed: Mar. 23, 2004

(65) Prior Publication Data

US 2004/0236358 A1  Nov. 25, 2004

Related U.S. Application Data

(60) Provisional application No. 60/461,086, filed on Apr. 7, 2003.

(51) Int. Cl.
*A61F 9/00* (2006.01)
(52) U.S. Cl. .................................... 606/166; 606/171
(58) Field of Classification Search ................ 606/161, 606/166, 171; 83/597, 601, 604, 605, 630, 83/632
See application file for complete search history.

(56) References Cited

U.S. PATENT DOCUMENTS

| | | | |
|---|---|---|---|
| 679,779 A | 8/1901 | Pierpont | |
| 727,396 A | 5/1903 | Luhrman | |
| 936,667 A | 10/1909 | Reynolds | |
| 1,092,367 A | 4/1914 | Knapp | |
| 1,400,379 A | 12/1921 | Schollmeyer | |
| 1,440,325 A | 12/1922 | Wilhelm | |
| 1,617,924 A | 2/1927 | Russell | |
| 1,660,134 A | 2/1928 | Mernit | |
| 1,761,260 A | 6/1930 | Gallasch | |
| 1,896,828 A | 2/1933 | Nichterlein | |
| 1,974,606 A | 9/1934 | Fassin | |
| 2,015,160 A | 9/1935 | Shaler | |
| 2,457,772 A | 12/1948 | Brown et al. | |
| 2,486,645 A | 11/1949 | Hager | |
| 2,539,597 A | 1/1951 | Staples | |
| 2,648,138 A | 8/1953 | Gase | |

(Continued)

FOREIGN PATENT DOCUMENTS

AU  706115  6/1999

(Continued)

OTHER PUBLICATIONS

Barraquer, "Keratomeleusis," International Surgery, vol. 48, No. 2, pp. 103-117, Aug. 1967. (Incomplete).

(Continued)

*Primary Examiner*—Todd E Manahan
*Assistant Examiner*—Michael G Mendoza
(74) *Attorney, Agent, or Firm*—Harness, Dickey & Pierce, P.L.C.

(57) ABSTRACT

A microkeratome 10 for use in ophthalmic surgery includes a bar-link drive 20 connected to a cutting-head 36. A fixation ring 34 attaches to a patient's eye and is coupled to the bar-link drive 20 to the drive the cutting-head 36 at least partially across the fixation ring 34.

29 Claims, 8 Drawing Sheets

U.S. PATENT DOCUMENTS

| | | |
|---|---|---|
| 2,697,433 A | 12/1954 | Zehnder |
| 2,912,843 A | 11/1959 | Williams |
| 3,025,598 A | 3/1962 | Nissen |
| 3,074,407 A | 1/1963 | Moon et al. |
| 3,111,872 A | 11/1963 | Trippler |
| 3,167,868 A | 2/1965 | Arneson |
| 3,217,416 A | 11/1965 | Bachert et al. |
| 3,231,982 A | 2/1966 | Ribich |
| 3,316,635 A | 5/1967 | Merrow et al. |
| 3,331,650 A | 7/1967 | Williams |
| 3,412,732 A | 11/1968 | Simon |
| 3,428,045 A | 2/1969 | Kratzsch et al. |
| 3,508,835 A | 4/1970 | Ware |
| 3,535,793 A | 10/1970 | Williams et al. |
| 3,554,197 A | 1/1971 | Dobie |
| 3,577,637 A | 5/1971 | Braginetz |
| 3,583,403 A | 6/1971 | Pohl et al. |
| 3,606,550 A | 9/1971 | Proska |
| 3,701,199 A | 10/1972 | Lewis |
| 3,708,881 A | 1/1973 | Bennett |
| 3,846,008 A | 11/1974 | Sobajima et al. |
| 3,879,847 A | 4/1975 | Roll |
| 3,905,374 A | 9/1975 | Winter |
| 4,173,980 A | 11/1979 | Curtin |
| 4,180,075 A | 12/1979 | Marinoff |
| 4,205,682 A | 6/1980 | Crock et al. |
| 4,207,790 A | 6/1980 | Endo |
| 4,211,232 A | 7/1980 | Mormann et al. |
| 4,265,023 A | 5/1981 | Frost et al. |
| 4,271,740 A | 6/1981 | Yamazaki et al. |
| 4,298,004 A | 11/1981 | Schachar et al. |
| 4,329,785 A | 5/1982 | Peterson |
| 4,393,587 A | 7/1983 | Kloosterman |
| 4,414,749 A | 11/1983 | Johannsmeier |
| 4,423,728 A | 1/1984 | Lieberman |
| 4,429,696 A | 2/1984 | Hanna |
| 4,438,567 A | 3/1984 | Raiha |
| 4,452,235 A | 6/1984 | Reynolds |
| 4,489,489 A | 12/1984 | Sarto |
| 4,490,885 A | 1/1985 | Iskiw et al. |
| 4,495,701 A | 1/1985 | Nakadoi |
| 4,499,898 A | 2/1985 | Knepshield et al. |
| 4,517,741 A | 5/1985 | Castelluzzo |
| 4,526,171 A | 7/1985 | Schachar |
| 4,538,356 A | 9/1985 | Knepshield et al. |
| 4,546,773 A | 10/1985 | Kremer et al. |
| 4,565,198 A | 1/1986 | Koeniger |
| 4,598,714 A | 7/1986 | Kremer et al. |
| 4,607,617 A | 8/1986 | Choyce |
| 4,619,259 A | 10/1986 | Graybill et al. |
| 4,630,378 A | 12/1986 | Kulp et al. |
| 4,637,393 A | 1/1987 | Ray |
| 4,642,892 A | 2/1987 | Ishida |
| 4,648,400 A | 3/1987 | Schneider et al. |
| 4,660,556 A | 4/1987 | Swinger et al. |
| 4,662,075 A | 5/1987 | Mastel et al. |
| 4,662,370 A | 5/1987 | Hoffmann et al. |
| 4,662,881 A | 5/1987 | Nordan |
| 4,665,914 A | 5/1987 | Tanne |
| 4,671,276 A | 6/1987 | Reynolds |
| 4,672,964 A | 6/1987 | Dee et al. |
| 4,674,503 A | 6/1987 | Peyman et al. |
| 4,676,790 A | 6/1987 | Kern |
| 4,688,570 A | 8/1987 | Kramer et al. |
| 4,718,418 A | 1/1988 | L'Esperance, Jr. |
| 4,723,545 A | 2/1988 | Nixon et al. |
| 4,744,144 A | 5/1988 | Lowery, Sr. et al. |
| 4,750,489 A | 6/1988 | Berkman et al. |
| 4,750,491 A | 6/1988 | Kaufman et al. |
| 4,766,895 A | 8/1988 | Reynolds |
| 4,768,509 A | 9/1988 | Grosvenor et al. |
| 4,788,976 A | 12/1988 | Dee |
| 4,796,623 A | 1/1989 | Krasner et al. |
| 4,807,623 A | 2/1989 | Lieberman |
| 4,813,132 A | 3/1989 | Castelluzzo |
| 4,815,218 A | 3/1989 | Gordy |
| 4,815,463 A | 3/1989 | Hanna |
| 4,821,357 A | 4/1989 | Millette |
| 4,826,042 A | 5/1989 | Vujovich |
| 4,834,748 A | 5/1989 | McDonald |
| 4,835,865 A | 6/1989 | Knoop |
| 4,840,175 A | 6/1989 | Peyman |
| 4,844,070 A | 7/1989 | Dee |
| 4,865,033 A | 9/1989 | Krumeich et al. |
| 4,884,569 A | 12/1989 | Fedorov et al. |
| 4,884,570 A | 12/1989 | Krumeich et al. |
| 4,898,170 A | 2/1990 | Hofmann et al. |
| 4,900,300 A | 2/1990 | Lee |
| 4,903,695 A | 2/1990 | Warner et al. |
| 4,914,816 A | 4/1990 | Fenn et al. |
| 4,917,086 A | 4/1990 | Feltovich et al. |
| 4,943,296 A | 7/1990 | Funakubo et al. |
| 4,994,081 A | 2/1991 | Civerchia et al. |
| 4,997,437 A | 3/1991 | Grieshaber |
| 5,007,169 A | 4/1991 | Motta |
| 5,009,660 A | 4/1991 | Clapham |
| 5,011,498 A | 4/1991 | Krumeich et al. |
| 5,055,106 A | 10/1991 | Lundgren |
| 5,063,942 A | 11/1991 | Kilmer et al. |
| 5,084,059 A | 1/1992 | Metzger |
| 5,092,863 A | 3/1992 | Schanzlin |
| 5,105,545 A | 4/1992 | Fletcher |
| 5,108,412 A | 4/1992 | Krumeich et al. |
| 5,112,350 A | 5/1992 | Civerchia et al. |
| 5,133,726 A | 7/1992 | Ruiz et al. |
| 5,139,518 A | 8/1992 | White |
| 5,152,786 A | 10/1992 | Hanna |
| 5,171,254 A | 12/1992 | Sher |
| 5,178,626 A | 1/1993 | Pappas |
| 5,188,125 A | 2/1993 | Kilmer et al. |
| 5,201,747 A | 4/1993 | Mastel |
| 5,203,865 A | 4/1993 | Siepser |
| 5,215,104 A | 6/1993 | Steinert |
| 5,217,477 A | 6/1993 | Lager |
| 5,222,960 A | 6/1993 | Poley |
| 5,222,967 A | 6/1993 | Casebeer et al. |
| 5,222,976 A | 6/1993 | Yoon |
| 5,224,950 A | 7/1993 | Prywes |
| 5,226,905 A | 7/1993 | Hanna |
| 5,232,568 A | 8/1993 | Parent et al. |
| 5,269,795 A | 12/1993 | Arnott |
| 5,288,292 A | 2/1994 | Giraud et al. |
| 5,290,301 A | 3/1994 | Lieberman |
| 5,299,354 A | 4/1994 | Metcalf et al. |
| 5,306,282 A | 4/1994 | Muller |
| 5,308,355 A | 5/1994 | Dybbs |
| 5,312,394 A | 5/1994 | Beckman |
| 5,318,044 A | 6/1994 | Kilmer et al. |
| 5,318,046 A | 6/1994 | Rozakis |
| 5,336,235 A | 8/1994 | Myers |
| 5,336,236 A | 8/1994 | Nevyas-Wallace |
| 5,337,482 A | 8/1994 | Schmidt |
| 5,342,377 A | 8/1994 | Lazerson |
| 5,342,378 A | 8/1994 | Giraud et al. |
| 5,352,233 A | 10/1994 | Anis |
| 5,368,604 A | 11/1994 | Kilmer et al. |
| 5,370,652 A | 12/1994 | Kellan |
| 5,376,099 A | 12/1994 | Ellis et al. |
| 5,395,385 A | 3/1995 | Kilmer et al. |
| 5,403,335 A | 4/1995 | Loomas et al. |
| 5,405,355 A | 4/1995 | Peyman et al. |
| 5,411,510 A | 5/1995 | Fugo |
| 5,411,511 A | 5/1995 | Hall |
| 5,423,840 A | 6/1995 | Casebeer et al. |

| | | | | | | |
|---|---|---|---|---|---|---|
| 5,423,841 | A | 6/1995 | Kornefeld | 6,022,364 | A | 2/2000 | Flumene et al. |
| 5,431,671 | A | 7/1995 | Nallakrishnan | 6,022,365 | A | 2/2000 | Aufaure et al. |
| 5,437,657 | A | 8/1995 | Epstein | 6,030,398 | A | 2/2000 | Klopotek |
| 5,441,511 | A | 8/1995 | Hanna | 6,033,075 | A | 3/2000 | Fujieda et al. |
| 5,441,512 | A | 8/1995 | Muller | 6,033,418 | A | 3/2000 | Gordon et al. |
| 5,447,517 | A | 9/1995 | Steen et al. | 6,036,709 | A | 3/2000 | Boutros |
| 5,458,610 | A | 10/1995 | Feaster | 6,042,594 | A | 3/2000 | Hellenkamp |
| 5,464,417 | A | 11/1995 | Eick | 6,045,562 | A | 4/2000 | Amano et al. |
| 5,486,188 | A | 1/1996 | Smith | 6,051,009 | A | 4/2000 | Hellenkamp et al. |
| 5,489,299 | A | 2/1996 | Schachar | 6,056,764 | A | 5/2000 | Smith |
| 5,496,339 | A | 3/1996 | Koepnick | 6,059,805 | A | 5/2000 | Sugimura et al. |
| 5,507,741 | A | 4/1996 | L'Esperance, Jr. | 6,071,293 | A | 6/2000 | Krumeich |
| 5,507,759 | A | 4/1996 | Nordan | 6,080,166 | A | 6/2000 | McEwen et al. |
| 5,527,328 | A | 6/1996 | Pintucci | 6,083,236 | A | 7/2000 | Feingold |
| 5,529,581 | A | 6/1996 | Cusack | 6,090,119 | A | 7/2000 | Pierce et al. |
| 5,545,172 | A | 8/1996 | Knepshield et al. | 6,099,541 | A | 8/2000 | Klopotek |
| 5,549,139 | A | 8/1996 | Perkins et al. | 6,117,149 | A | 9/2000 | Sorensen et al. |
| 5,549,622 | A | 8/1996 | Ingram | 6,126,668 | A | 10/2000 | Bair et al. |
| 5,556,406 | A | 9/1996 | Gordon et al. | 6,132,446 | A | 10/2000 | Hellenkamp et al. |
| 5,562,691 | A | 10/1996 | Tano et al. | 6,136,012 | A | 10/2000 | Chayet et al. |
| 5,562,693 | A | 10/1996 | Devlin et al. | 6,139,559 | A | 10/2000 | Nordan et al. |
| 5,571,124 | A | 11/1996 | Zelman | 6,139,560 | A | 10/2000 | Kremer |
| 5,586,980 | A | 12/1996 | Kremer et al. | 6,143,011 | A | 11/2000 | Hood et al. |
| RE35,421 | E | 1/1997 | Ruiz et al. | 6,149,609 | A | 11/2000 | Lieberman et al. |
| 5,591,174 | A | 1/1997 | Clark et al. | 6,149,661 | A | 11/2000 | Graczyk |
| 5,591,185 | A | 1/1997 | Kilmer et al. | 6,165,189 | A | 12/2000 | Ziemer |
| 5,595,570 | A | 1/1997 | Smith | 6,176,853 | B1 | 1/2001 | Stolyarenko |
| 5,603,365 | A | 2/1997 | Stewart | 6,183,488 | B1 | 2/2001 | Ross et al. |
| 5,619,889 | A | 4/1997 | Jones et al. | 6,185,823 | B1 | 2/2001 | Brown et al. |
| 5,620,453 | A | 4/1997 | Nallakrishnan | 6,197,038 | B1 | 3/2001 | O'Donnell, Jr. |
| 5,624,456 | A | 4/1997 | Hellenkamp | 6,203,555 | B1 | 3/2001 | Amano et al. |
| 5,632,757 | A | 5/1997 | Arnott | 6,228,099 | B1 | 5/2001 | Dybbs |
| 5,634,918 | A | 6/1997 | Richards | 6,231,583 | B1 | 5/2001 | Lee |
| 5,643,299 | A | 7/1997 | Bair | 6,254,619 | B1 | 7/2001 | Garabet et al. |
| 5,658,303 | A | 8/1997 | Koepnick | 6,258,110 | B1 | 7/2001 | Hellenkamp |
| 5,662,668 | A | 9/1997 | Kurwa | 6,277,134 | B1 * | 8/2001 | Amano et al. ................ 606/166 |
| 5,669,144 | A | 9/1997 | Hahn et al. | 6,296,649 | B1 | 10/2001 | Hellenkamp |
| 5,674,233 | A | 10/1997 | Dybbs | 6,387,107 | B1 | 5/2002 | Hellenkamp |
| 5,683,592 | A | 11/1997 | Bartholomew et al. | 6,514,266 | B2 * | 2/2003 | Farris et al. ................. 606/166 |
| 5,690,123 | A | 11/1997 | Medina | 6,527,788 | B1 | 3/2003 | Hellenkamp |
| 5,690,641 | A | 11/1997 | Sorensen et al. | 6,641,594 | B2 * | 11/2003 | Aufaure et al. .............. 606/166 |
| 5,690,657 | A | 11/1997 | Koepnick | 2002/0082628 | A1 | 6/2002 | Hellenkamp |
| 5,695,509 | A | 12/1997 | El Hage | 2002/0091401 | A1 | 7/2002 | Hellenkamp |
| 5,700,274 | A | 12/1997 | Feaster | 2003/0060840 | A1 | 3/2003 | Aufaure et al. .............. 606/166 |
| 5,222,967 | A | 1/1998 | Casebeer et al. | | | | |
| 5,713,915 | A | 2/1998 | Van Heugten et al. | | | | |
| 5,733,334 | A | 3/1998 | Lee | | | | |
| 5,772,675 | A | 6/1998 | Hellenkamp | | | | |
| 5,779,723 | A * | 7/1998 | Schwind .................... 606/166 | | | | |
| 5,792,161 | A | 8/1998 | de Almeida Cunha | | | | |
| 5,807,380 | A | 9/1998 | Dishler | | | | |
| 5,807,381 | A | 9/1998 | Lieberman | | | | |
| 5,810,857 | A | 9/1998 | Mackool | | | | |
| 5,817,115 | A | 10/1998 | Nigam | | | | |
| 5,833,701 | A | 11/1998 | Gordon | | | | |
| 5,855,604 | A | 1/1999 | Lee | | | | |
| 5,857,995 | A | 1/1999 | Thomas et al. | | | | |
| 5,871,492 | A | 2/1999 | Sorensen | | | | |
| 5,873,881 | A | 2/1999 | McEwen et al. | | | | |
| 5,876,415 | A | 3/1999 | Pierce et al. | | | | |
| 5,876,439 | A | 3/1999 | Lee | | | | |
| 5,934,285 | A | 8/1999 | Kritzinger et al. | | | | |
| 5,935,140 | A | 8/1999 | Buratto | | | | |
| 5,944,731 | A | 8/1999 | Hanna | | | | |
| 5,947,987 | A | 9/1999 | Gordon et al. | | | | |
| 5,964,748 | A | 10/1999 | Peyman | | | | |
| 5,964,775 | A | 10/1999 | Gordon et al. | | | | |
| 5,964,776 | A | 10/1999 | Peyman | | | | |
| 5,976,163 | A | 11/1999 | Nigam | | | | |
| 5,980,543 | A | 11/1999 | Carriazo et al. | | | | |
| 5,989,272 | A | 11/1999 | Barron et al. | | | | |
| 5,997,559 | A | 12/1999 | Ziemer | | | | |
| 6,007,553 | A | 12/1999 | Hellenkamp et al. | | | | |

FOREIGN PATENT DOCUMENTS

| | | |
|---|---|---|
| BR | PI9707374-1 | 7/2000 |
| CN | 1089824 | 7/1994 |
| DE | 28 180 73 A1 | 10/1978 |
| DE | 31 476 62 A1 | 6/1983 |
| DE | 34 335 81 A1 | 3/1986 |
| DE | 38 255 87 A1 | 2/1990 |
| DE | 40 128 82 A1 | 10/1991 |
| EP | 0 261 242 A1 | 3/1988 |
| EP | 0 442 156 A1 | 8/1991 |
| EP | 0 442 156 B1 | 8/1991 |
| EP | 0 531 756 A2 | 3/1993 |
| EP | 0 555 625 A1 | 8/1993 |
| EP | 0 873 735 A1 | 10/1998 |
| EP | 0 900 554 A1 | 9/1999 |
| FR | 1 366 323 | 7/1964 |
| FR | 2 660 547 | 10/1991 |
| FR | 2 693 368 | 1/1994 |
| FR | 2 751 206 | 1/1998 |
| FR | 0013067 | 10/2000 |
| FR | 0105228 | 4/2001 |
| GB | 2 129 957 A | 3/1980 |
| GB | 2 092 008 A1 | 8/1982 |
| GB | 2 095 119 A | 9/1982 |
| GB | 2 113 550 A | 8/1983 |
| GB | 2 178 324 A | 2/1987 |
| GB | 2 179 859 A | 3/1987 |

| | | | |
|---|---|---|---|
| GB | 2 242 835 A | 10/1991 | |
| GB | 2 247 174 A | 2/1992 | |
| SG | 56167 | 8/2000 | |
| SG | 68725 | 1/2002 | |
| SU | 1463253 A1 | 3/1989 | |
| SU | 1657180 A1 | 6/1991 | |
| SU | 1685417 A1 | 10/1991 | |
| WO | WO 82/00759 | 3/1982 | |
| WO | WO 87/05799 | 10/1987 | |
| WO | WO 93/06783 | 4/1993 | |
| WO | WO 93/09738 | 5/1993 | |
| WO | WO 94/01067 | 1/1994 | |
| WO | WO 95/31143 | 11/1995 | |
| WO | WO 96/13216 | 5/1996 | |
| WO | WO 98/27901 | 7/1998 | |
| WO | WO 99/26568 | 6/1999 | |
| WO | WO 00/56222 | 9/2000 | |
| WO | WO 01/93791 A1 | 12/2001 | |

OTHER PUBLICATIONS

Barraquer, "Lamellar Keratoplasty (Special Techniques)," Annals of Ophthalmology, pp. 437-469, Jun. 1972. (Incomplete).
Barraquer, "Queratomileusis y Queratofaquia," 1980.
Barraquer, "Keratomileusis for Myopia and Aphakia," Ophthalmology, vol. 88, No. 8, pp. 701-708, Aug. 1981.
Barraquer, "Results of Hypermetropic Keratomileusis, 1980-1981," Steinway Instrument Co., pp. 25-44.
Bores Eye Institute, "Lamellar Refractive Keratoplasty," Ch. 4, pp. 1-9, 1988, 1989.
Burillon et al., "Combined Epikeratoplasty and Homoplastic-Keratophakia for Correction of Aphakia: Double Curve Effect," Refractive & Corneal Surgery, vol. 9, pp. 214-218, May/Jun. 1993.
Casebeer et al., "Lamellar Refractive Surgery," SLACK Inc., Ch. 3, pp. 41-56, 1996.
Chiron Intraoptics, Refractive Surgery Catalog, 1992.
Chiron Vision Corp., "Automatic Corneal Shaper™ Operator's Manual," Rev. 1.4, Jul. 1994.
Clayman et al., "Intraocular Lens Implantation Techniques and Complications," The C.V. Mosby Company, p. 38, 1983.
Draeger, "A Semi-Automatic Electric Ketatome for Lamellar Corneal Graft," Klin. Mbl. Augenheilk, 167, pp. 353-359, 1975.
Draeger et al., "New Methods in Refractive Corneal Surgery—An Experimental Study," Klin. Mbl. Augenheilk, 192, pp. 458-461, 1988.
G&G Medical Instruments, Ltd., The MARINOFF Calibration-Inspection RK Microscope, Advertisement.
Hanna et al., "Keratotomy for Astigmatism Using an Arcuate Keratome," Archives of Opthalmology, vol. 111, No. 7, pp. 998-1004, Jul. 1993. (Abstract Only).
Hanna et al., "Keratotomy for Astigmatism Using an Arcuate Keratome," Archives of Ophthalmology, vol. 111, No. 7, pp. 998-1004, Jul. 1993.
Hofmann et al., "An Independent Evaluation of Second Generation Suction Microkeratomes," Refractive & Corneal Surgery, vol. 8, No. 5, pp. 348-354, Sep./Oct. 1992. (Abstract Only).
Jones, "The Optical Micrometer," Optical Engineering, vol. 15, No. 3, pp. 247-250, May/Jun. 1976.
Kohlhass et al., "Keratomileusis With a Lamellar Microkeratome and the Eximer Laser," Ophthalmologe, 92(4):499-502, Aug. 1995. (Abstract Only).
Kremer, "ALK-E: As Good as Advertised," Review of Ophthalmology, Aug. 1994.
Kronemyer, "Advanced Microkeratome Simplifies ALK," Slack Inc., Jan. 1996, 1998.
Microtech, Inc., Video Newsletter, vol. 1, Issue 2, Spring 1995.
Nordan, "Keratomileusis " Refractive Keratoplasty, pp. 1-12, 1987.
Pallikaris et al., "Excimer Laser in Situ Keratomileusis and Photorefractive Keratectomy for Correction of High Myopia," Journal of Refractive & Corneal Surgery, vol. 10, pp. 498-510, Sep./Oct. 1994. (Incomplete).

Pouliquen et al., "The Hanna Radial Microkeratome: Presentation and First Experiment," Dev. Opthalmology, 14:132-136, 1987. (Abstract Only).
Rozakis, editor, "Refractive Lamellar Keratoplasty," SLACK Inc., Chs. 1-2, 5-10, and 13, 1994.
Ruiz, "Flap and Zap: Is The Next Radial K?," Review of Opthalmology, Aug. 1994.
Smith, "SCMD Keratome Unit," Refractive & Corneal Surgery, vol. 6, p. 207, May/Jun. 1990.
Steinway Instrument Company, Inc., "The Steinway/Barraquer In-Situ Microkeratome Set," Brochure.
Stonecipher et al., "Refractive Corneal Surgery with the Draeger Rotary Microkeratome in Human Cadaver Eyes," Journal of Refractive & Corneal Surgery, 10(1):49-55, Jan./Feb. 1994. (Abstract Only).
Stortz Instrument Company, Eye Instrument Catalog, Twelfth Ed., 1973.
Wilson et al., "Corrective Measures for Myopia," Survey of Opthalmology, vol. 34, No. 4, pp. 294-304, Jan./Feb. 1990. (Incomplete).
Moria, "Carriazo Barraquer Lamellar System for Keratoplasty" Brochure, V1.
Moria, "Carriazo Barraquer Lamellar System for Keratoplasty" Brochure, V2.
Moria, "Carriazo-Barraquer LSK" Brochure, 1998, V1.
Moria, "Carriazo-Barraquer LSK" Brochure, 1998, V2.
Barraquer, Editor, "Refractive Keratoplasty (Compilation of Reprints) vol. 1," Instituto Barraquer de America, Bogata, Columbia, Mar. 1970.
Buratta et al., Editors, "LASIK Principles and Techniques," SLACK Inc., Chs. 4, 6-7, 12-13, 23-24, 26-27, and 33, 1998.
Buratta et al., Editors, "LASIK Surgical Techniques and Complications," SLACK Inc., Chs. 4-8, and 13-20, 2000.
Gimbel et al., "LASIK Complications: Prevention and Management," SLACK, Inc., Chs. 3-5, and 9, 1999.
Machat, "Excimer Laser Refractive Surgery," SLACK Inc., Chs. 8, 10, 12, and Appendices, 1996.
Microtech, Inc., Moria LASIK "One" Microkeratome Product, Informtion, Bate Stamp Nos. BLOA0045563-BLOA004556, http://www.microtechnic.com.[1].
Moria, LASIK "One" Microkeratome Product Information, Bate Stamp No. BLOA017127, http://www.moria-surgical.com, (accessed Oct. 20, 2000).
Moria, LASIK "One" Microkeratome Product Information, Bate Stamp Nos. BLOA021123-BLOA021137, http://www.moria-surgical.com, (accessed Oct. 20, 2000).
Moria, "LSK ONE Instruction Manual LSK-Classic "ONE" Microkeratome Head," Version ME-LKS ONE-VA-19/8/97, Bate Stamp Nos. OM20790-OM20826, 1997.
Moria, "LSK ONE Instruction Manual LSK-Classic "ONE" Microkeratome Head," Version ME-LKS ONE-VA-19/8/97, Bate Stamp Nos. MORIA003830-MORIA003868, 1997. (Alternate Version).
Moria, "LSK ONE Instruction Manual Part 2/2 •LSK-ONE Microkeratome Head and Accessories," Version ME-ONE-VA-08/06/00, Bate Stamp Nos. MORIA000827-MORIA000852, 2000.
Moria, LSK One Microkeratome Product Brochure, Bate Stamp Nos. BL001108-BL001111.
Rozakis, "Refractive Lamellar Keratoplasty," SLACK Inc., 1994.[2].
Singer, "Adjustable Power and Positioning Options Define New Microkeratome," Ocular Surgery News, vol. 16, No. 21, Nov. 1, 1998, Reprinted by SLACK Inc., 1998.
Singer, "Adjustable Power and Positioning Options Define New Microkeratome," Ocular Surgery News, vol. 16, No. 21, Nov. 1, 1998, Reprinted by SLACK Inc., 1998. (Alternative Version).

* cited by examiner

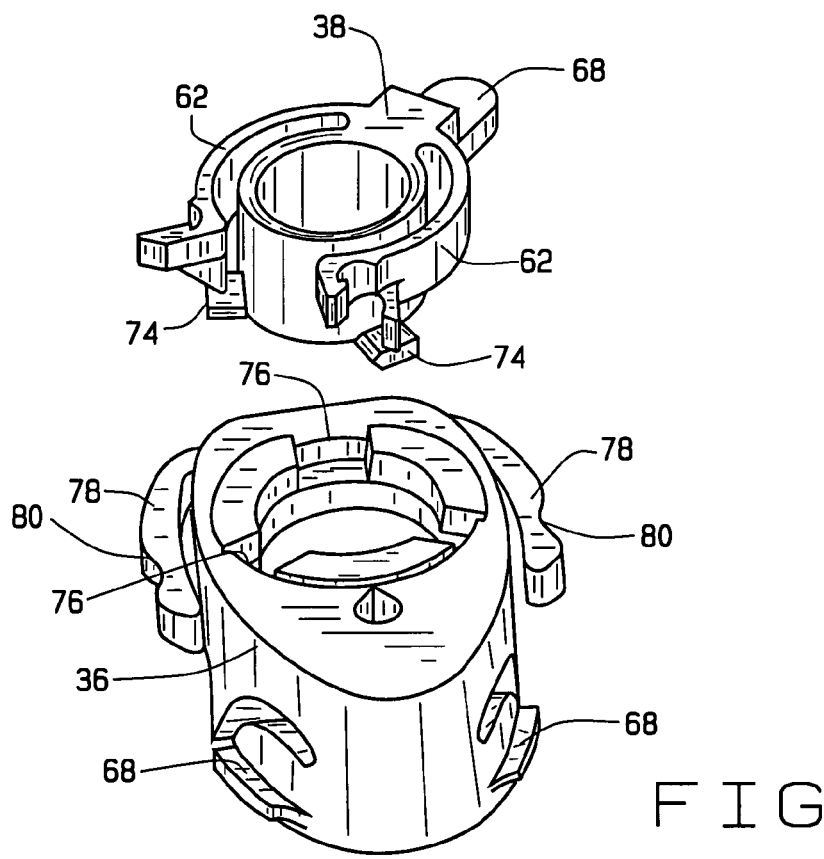
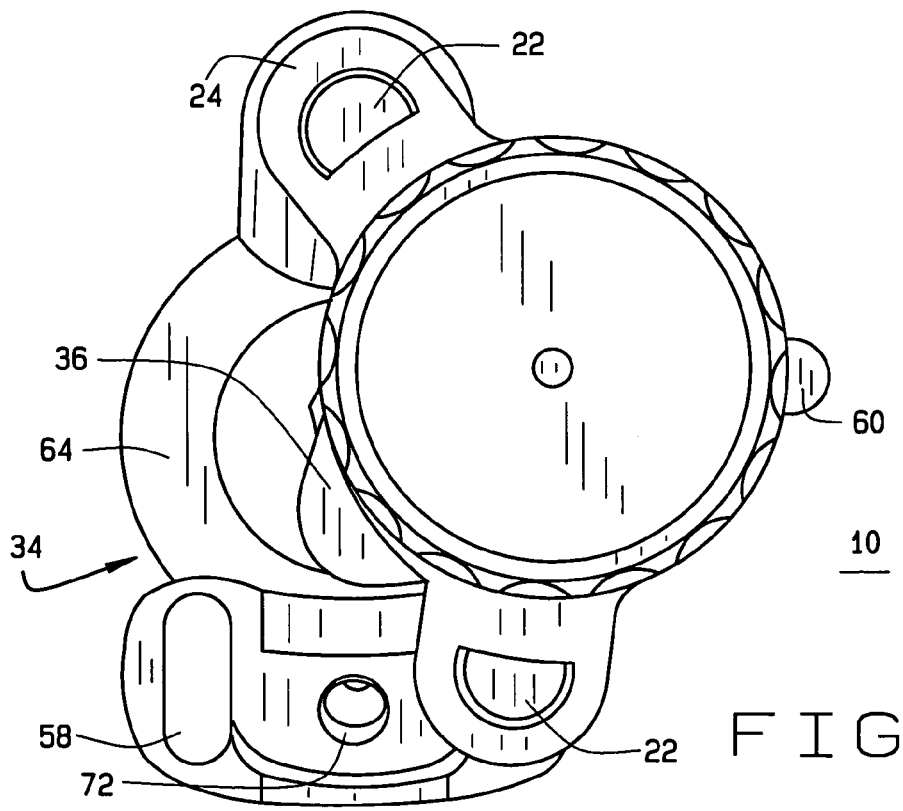

BAR-LINK DRIVE SYSTEM FOR A MICROKERATOME

Priority is hereby claimed in the present nonprovisional application to Provisional Application Ser. No. 60/461,086 filed Apr. 7, 2003, in accordance with 37 CFR 1.78(a)(4).

BACKGROUND OF THE INVENTION

1. Field of the Invention

The present invention is directed to a medical device used during eye surgery. In particular, the present invention is directed towards a microkeratome for cutting a cornea of a patient's eye and creating a flap of corneal tissue.

2. Description of Related Art

Laser-assisted in-situ keratomileusis or LASIK surgery has become a fairly common procedure for correcting refractive errors in a patient's sight. Such LASIK surgery may eliminate or greatly reduce the need for the patient to use eyeglasses or contact lenses.

In LASIK surgery, a laser ablates a certain amount of corneal tissue to change the curvature of the cornea in order to reduce or eliminate the refractive errors inherently contained in the cornea. Before such laser ablation occurs in the LASIK procedure, a corneal flap is commonly formed with an instrument known as a microkeratome. A microkeratome is well known in the art, and generally includes a blade that is manually pushed or mechanically driven along a path across a suction ring, which holds the cornea in place during operation of the microkeratome. It is also common to oscillate the cutting blade in a direction transverse to a direction of the cutting path.

Unlike initial microkeratomes that removed a slice of corneal tissue from the eye, microkeratomes used in LASIK surgery create a flap with a corneal hinge. In other words, the microkeratome does not remove corneal tissue from the eye, but rather creates a flap which remains connected to the cornea of the patient at a hinge. Initially this hinge was created nasally or on the side of the eye by microkeratomes that traveled in a straight path across the suction ring. This allowed the main body and motor of the microkeratome to extend temporally from the patient. In this way the microkeratome avoided any interference with a patient's cheek, eyebrow, or nose during creation of the flap.

Microkeratomes then developed so that the hinge could be formed superiorly or at the top of the eye (known as a superior hinge). This was made possible by such microkeratomes as described in U.S. Pat. No. 5,624,456 to Hellenkamp, which description is incorporated in its entirety by reference. Hellenkamp avoided interference with a patient's anatomy by designing the microkeratome to be built vertically with the motor and cutting-head assembly directly above the cutting blade and pivoting across the suction ring. This allowed a superior hinge to be formed on the patient's eye, which many physicians believe is preferable to a nasal hinge because the superior hinge aligns with the blinking of the eye. In addition, such compact vertical design would even allow a nasal hinge to be formed.

While one embodiment of the Hellenkamp microkeratome has been a very successful commercial product known as the Bausch & Lomb Hansatome™, certain improvements to it and other pivoting microkeratomes are desired. For instance, the gear-track of the Hansatome may lead to jamming if the gear-track of the suction ring and the gear of the cutting-head assembly are not perfectly matched or if debris becomes lodged in the gear teeth. Therefore, it would be desirable to eliminate any gearing between the suction ring and the microkeratome cutting-head. The gearing also makes it difficult to mass-produce suction rings and cutting-heads which are interchangeable, which is highly desired for servicing and repairing the microkeratomes.

Other prior art pivoting microkeratomes, such as those available from Moria S.A. and known as CB microkeratomes or M2 microkeratomes have attempted to move the gear-track. Essentially, a crown gear has been formed on top of the pivot point in place of the gear-track of the Hansatome and a worm/worm gear interconnects the motor and the crown gear. Again, because of the gear interface between the suction ring and the cutting-head assembly, jamming is likely to occur. In fact, jamming may be more likely to occur on the CB unit because the torque required to pivot the microkeratome about a central pivot point is greater than the torque required for the outer gear-track of the Hansatome. The M2 attempts to overcome this jamming problem of the CB by substituting two motors to perform the function of one. That is, one motor for pivoting and a second separate motor for oscillating the cutting blade, thereby having more power available to overcome any gearing mismatch. This is in contrast to the Hansatome and the CB, which both use one motor for both the functions of translating the microkeratome across the suction ring and for oscillating the blade.

It would be desirable to provide a robust microkeratome design, which uses a compact and less expensive single motor design and still eliminates or greatly reduces the potential for jamming to occur. A single motor design is less expensive and potentially more reliable than a design utilizing two (2) motors, such as the M2.

Other prior art microkeratomes have avoided the potential for jamming during translation of the microkeratome head across the suction ring by simply eliminating a translation motor, and thereby, creating a manual microkeratome device which relies on the surgeon to push or pivot the microkeratome across the suction ring manually. However, it is believed that the consistency of depth of cut is sacrificed by the manual microkeratomes as are known in the prior art, as the thickness of the corneal flap is directly related to the speed of movement of the cutting-head across the suction ring. In addition, such prior art manual microkeratomes require a much more significant learning curve on the part of the surgeon than the use of an automated microkeratome.

BRIEF DESCRIPTION OF DRAWINGS

FIG. 6 is an exploded perspective view of a cutting-head assembly and a quick connect mechanism in accordance with the present invention;

FIG. 7 is a top view of a microkeratome in accordance with the present invention;

DETAILED DESCRIPTION OF THE PREFERRED EMBODIMENT

Figure 1:
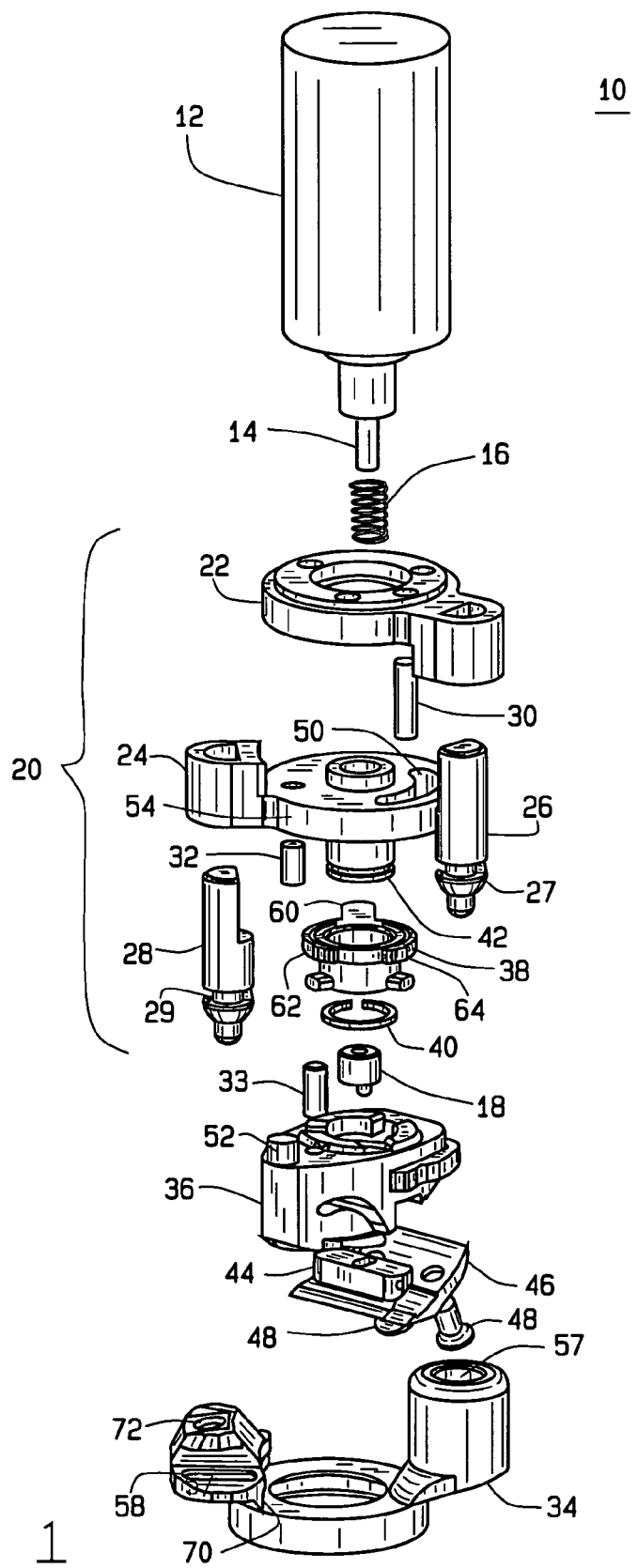
FIG. 1 shows an exploded perspective view of a microkeratome in accordance with the present invention.

A microkeratome 10 is shown in an exploded perspective view in FIG. 1. Microkeratome 10 preferably includes a motor gearbox 12 and a drive shaft 14. Preferably, motor gearbox 12 is a Maxon Model No. 118426, though other motor and/or gear combinations may be acceptable. Drive shaft 14 fits within compression spring 16 and preferably into blade eccentric drive head 18. An embodiment of a bar linkage or bar-link drive is shown generally at 20, and includes a top drive link or arm 22, a bottom drive arm 24, link pins 26 and 28, and dowel pins 30 and 32. As used herein, bar linkage or bar-link drive are intended to have their ordinary meaning as would be understood by a person of ordinary skill in the art. As will be recognized by a person of ordinary skill in the art, other embodiments with bar-link 20 having different configurations can be utilized in microkeratome 10. In use, as described in detailed below, bar-link drive 20 cooperates with suction ring 34 to form a four-bar-link drive which in one preferred embodiment forms a slider-crank mechanism. Drive mechanism 20 is preferably constructed of stainless steel.

A cutting-head 36 is preferably connected to drive 20 at link 24 with a snap-on connector 38 which requires less than 360° of rotation of the cutting-head 36 relative to the drive 20 for connection of the cutting-head, thereby resulting in a quick-connection of the cutting-head 36 to the drive 20. Cutting-head 36 is preferably formed of stainless steel. Cutting head 36 may comprise a unitary body or be formed from 2 or more pieces. Snap-on connector 38 is preferably connected to drive link 24 via retaining ring 40 being received in groove 42, though other connections are possible, such as screw threads, a spring snap, or an annular spring snap. Although other connectors can be used, utilizing snap-on connector 38 or another quick-connection embodiment avoids the cumbersome use of the prior art threaded connection. This allows a user to quickly assemble and disassemble the microkeratome 10, which can be a significant benefit in a busy operating room.

Microkeratome 10 utilizes a cutting blade assembly 44. Cutting blade assembly 44 is preferably similar to that described in U.S. Pat. No. 6,051,009 to Hellenkamp, et al., which is incorporated herein by reference. The cutting blade assembly comprises a blade and a blade holder secured to the blade. Although the blade can be a wide variety of configurations, such as rectangular, triangular, partially elliptical, partially circular, etc., preferably the width of the blade is decreased from the front to the rear to avoid interference with suction ring 34. Assembly 44 is held within cutting-head 36 by door 46 and screws 48. In operation, cutting blade assembly 44 is preferably oscillated by eccentric drive head 18 as the motor 12 drives bar-link drive 20 across suction ring 34.

Suction or fixation ring 34 is for attachment to a patient's eye (not shown) in a manner well known in the art and is preferably constructed of stainless steel. Ring 34 is preferably coupled to the bar-link drive 20 via drive link pins 26 and 28. Hence, bar-link drive 20, drives the cutting-head 36 at least partially across fixation ring 34 to form a corneal flap. The cutting blade assembly 44 is oscillated at a rate and driven across fixation ring 34 at a speed such as are commonly used in the prior art though various oscillation and drive speeds may be used. The blade preferably oscillates at approximately 7,200 cycles/minute and transverses across the eye at approximately 1.6 revolutions per minute. It is preferred to maintain this same ratio between the blade cycles and the traverse speed; therefore, if the ratio is maintained the speed may vary and still achieve acceptable precision. Dowel pin 30 preferably cooperates with slot 50 to limit the extent to which cutting-head 36 may be driven across fixation ring 34. Other means of restricting movement of cutting head 36, such as are known to those skilled in the art can be utilized. Pin 52 may also be used to cooperate with surface 54 to orient cutting-head 36 to the fixation ring 34 in a start position.

Figure 2:
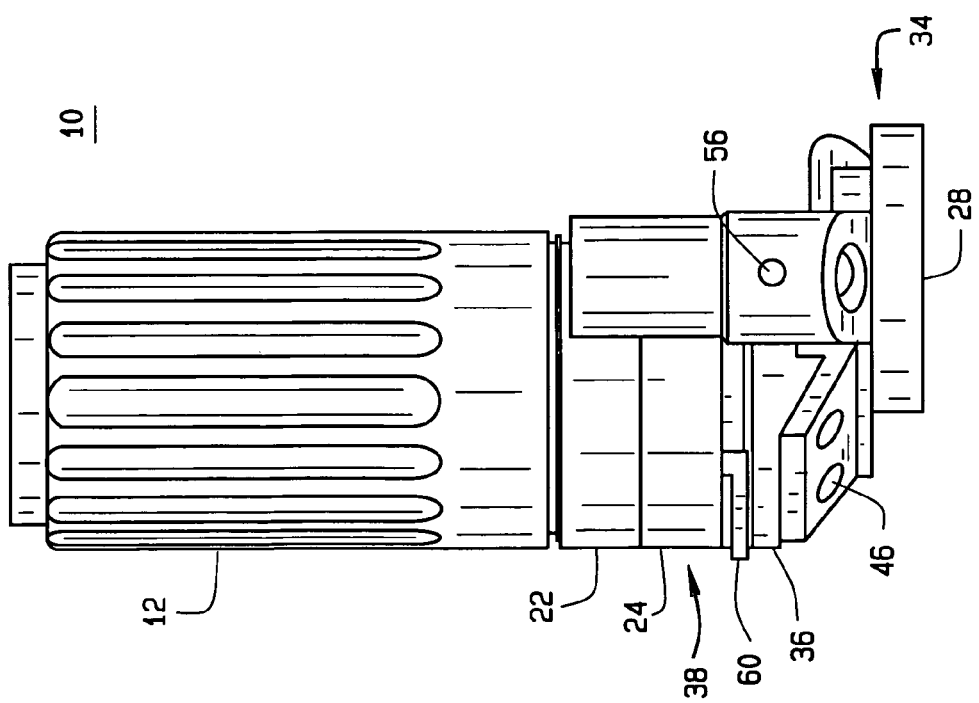
FIG. 2 is a side elevation view of a microkeratome in accordance with the present invention.

Dowel pins 32 and 33 preferably cooperate with snap-on connector 38 to act as a left or right eye selector, as described in detail below. FIG. 2 shows microkeratome 10 fully assembled, and in particular, shows the drive arms 22 and 24 that each include a fixation ring connection post 26 or 28. Each post or pin 26 and 28 preferably includes a slot 27 or 29, best seen at FIG. 1, such that the arm post 28 mates with an elevation pin 56, which extends within opening 57, shown in FIGS. 1 and 2. The other arm post 26 mates with a flange 59 of fixation ring 34, best seen in FIG. 3. A desirable and versatile feature of the present invention is that to form a flap on both eyes no disassembly and re-assembly of the microkeratome 10 is needed. Instead the user simply switches the position of posts 26 and 28 so that post 26 becomes the pivot point.

Advantageously, elevation pin 56 of the fixation ring 34 acts to hold the arm post 26 above a slot 58 of the fixation ring 34 to improve the ease of assembly of the drive 20 onto the fixation ring 34. Specifically, elevation pin 56 holds the arm post 26 or 28 above the slot 58 of the fixation ring 34 until the arm post 26 or 28 is above the slot 58 and in position to drop into slot 58.

Snap-on connector 38 includes a left/right selector comprising handle 60 and detent arms 62 and 64 for mating with dowel pins 32 and 33. The left/right selector is alternately moveable between a start position of the drive for a patient's left eye and start position for a patient's right eye. Specifically, the dowel pin 32 mates with detent arm 62 which is connected to drive arm 24, and thereby connects the motor 12 to drive arm 24, wherein connection post 28 becomes a pivot point of movement of the microkeratome 10. For the other eye, detent arm 64 mates with dowel pin 33 to connect drive arm 22 to the motor 12, thereby making connection post 26 the pivot point with relation to fixation ring 34.

Figure 3:
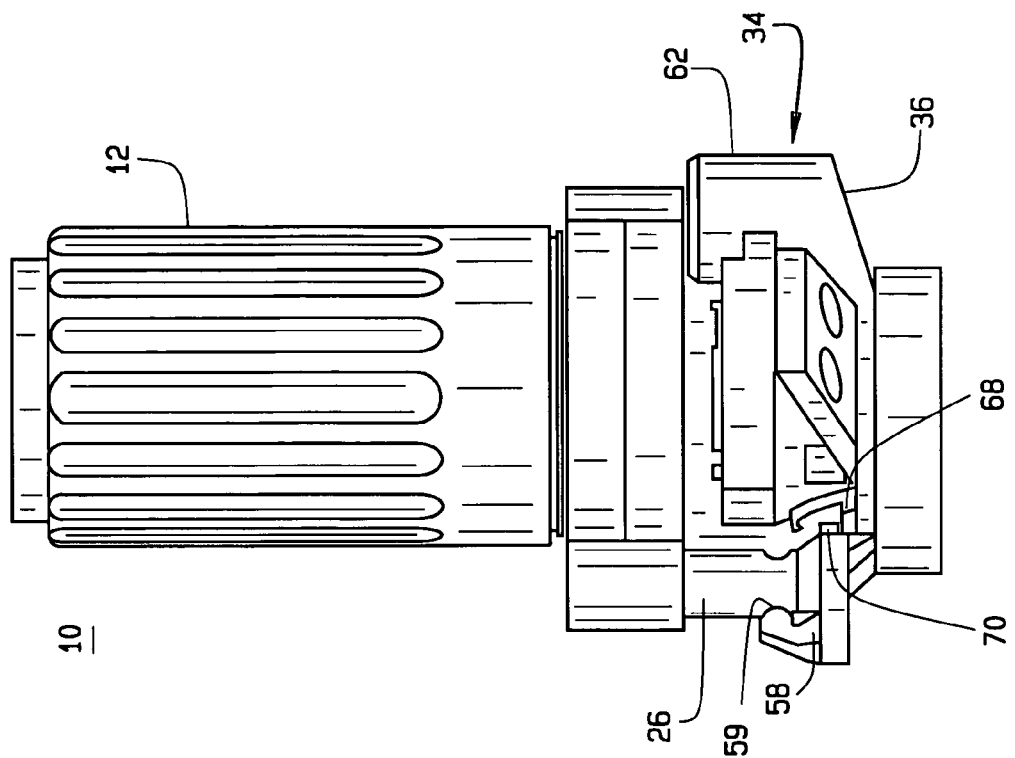
FIG. 3 is another side view.

Referring to FIG. 3, fixation ring 34 includes structure 62 forming the pivot hole 57, as well as structure forming slots 58 preferably on the opposing side of fixation ring 34 for causing the cutting-head 36 to move in an accurate path across the fixation ring, as described in further detail below.

Figure 4:
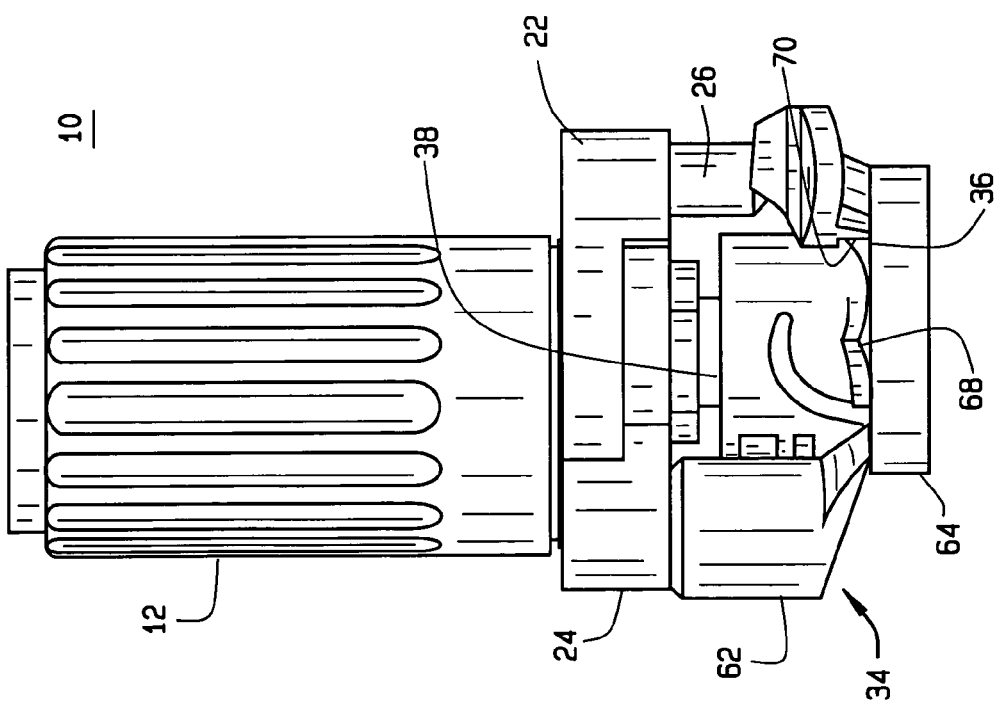
FIG. 4 is an elevation of the opposite side of FIG. 3.

Though the use of a pin 30 and slot 50 is preferably used to limit the length of translation of the cutting-head 36 across the fixation ring 34, it is possible that the length of slot 58 could be used to determine the length of translation of the drive 20 across the fixation ring 34. As can be easily seen in FIG. 4, fixation ring 34 preferably includes structure extending beyond and above a bottom-most part of annular ring 64 namely a pivot hole 57 and slots 58, such that the structure 62 forming pivot hole 57 and the slots 58 are raised above the bottom-most part of the annular ring for allowing the microkeratome 10 to be rotated about a patient's eye (not shown) without interference from the patient's anatomy namely the patient's nose, eyebrow, or cheek.

Figure 5:
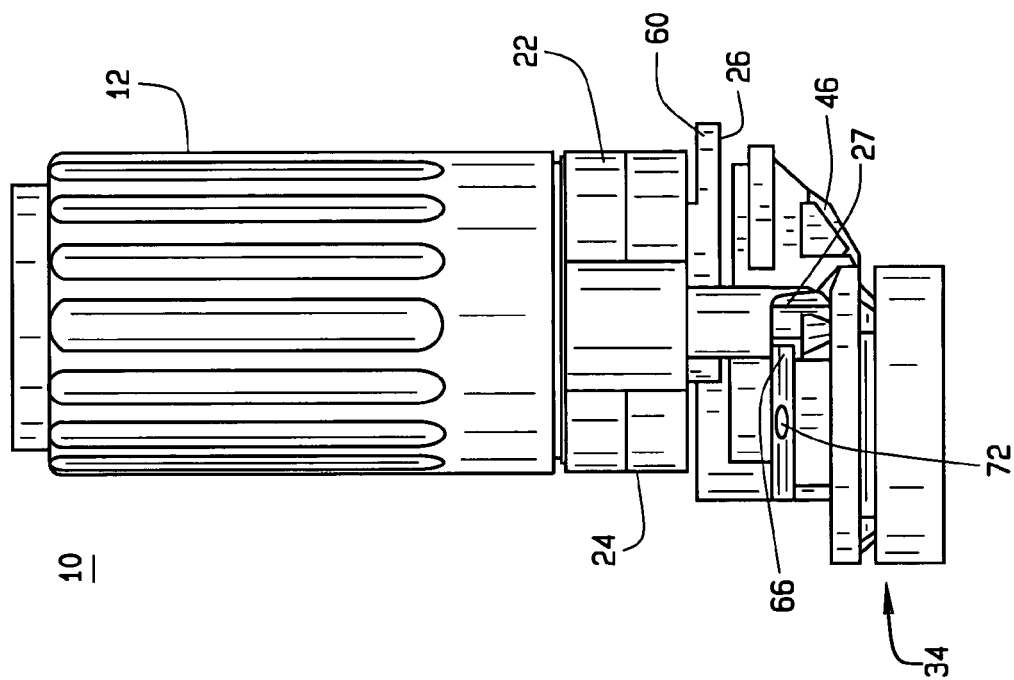
FIG. 5 is an elevation view of the opposite side of FIG. 2.

Referring to FIG. 5, grooves 27 or 29 mate with the elevation pins 56 or flange 66 of fixation ring 34 and, during operation of the microkeratome in ophthalmic surgery, cooperate to hold the motor and drive onto the suction ring 34, so that the microkeratome doesn't raise off of suction ring 34 as it is driven across a patient's eye. In addition, such slots cooperate to hold the microkeratome assembly level with respect to the suction ring 34 to prevent jamming during movement of the microkeratome across suction ring 34. Similarly, cutting-head 36 preferably includes flanges 68 on opposing sides for use with both the left and right eyes of a patient, which can be seen in FIGS. 1, 3, and 4. A flange 68 cooperates with a slot 70 of fixation ring 34 for assisting in holding the microkeratome onto fixation ring 34 and to hold the microkeratome level with respect to the fixation ring 34 again to maintain the microkeratome assembly level with respect to suction ring 34 to prevent jamming.

As can be seen in FIGS. 1 and 5, suction ring 34 also includes a passage 72 that mates with a suction post (not shown) so that fixation ring 34 may be affixed to a patient's eye as is well known in the art.

FIG. 6 shows an exploded perspective view of the cutting-head 36 and the snap-on connector 38. As can been seen, snap-on 38 preferably includes three arms 74 which mate with indents 76, such that cutting-head assembly 36 is quickly connected to snap-on connector 38 with less than one full 360° turn of cutting-head 36. FIG. 6 also provides a good view of detent arms 62 and 64 described above. Flanges 68 are also easily seen in FIG. 6. In addition, cutting-head 36 preferably includes cutting-head locator 78 for angularly positioning an axis of rotation of cutting-head 36 with respect to ring 34. Preferably, cutting-head locator 78 includes indents 80 on resilient spring-like arms as shown. Arms 78 and specifically indents 80 mate with structure 62 and are placed on opposite sides of the cutting-head for providing location for both the left and right eyes of the patient. Cutting-head locators 78 increase the rigidity and stability of rotational movement of the cutting-head 36 across fixation ring 34 during surgery, which further assists in preventing jamming of the microkeratome 10.

FIG. 7 is a top view of microkeratome 10, including drive arms 22 and 24 and shows passage 72 that is formed in suction ring 34 from a bottom surface of the annular ring 64 through a suction post (not shown) for connection to a vacuum source (not shown) such that the annular ring 64 may be affixed to the cornea of a patient by operation of the vacuum source. A good view of a slot 58 is also shown.

Figure 8:
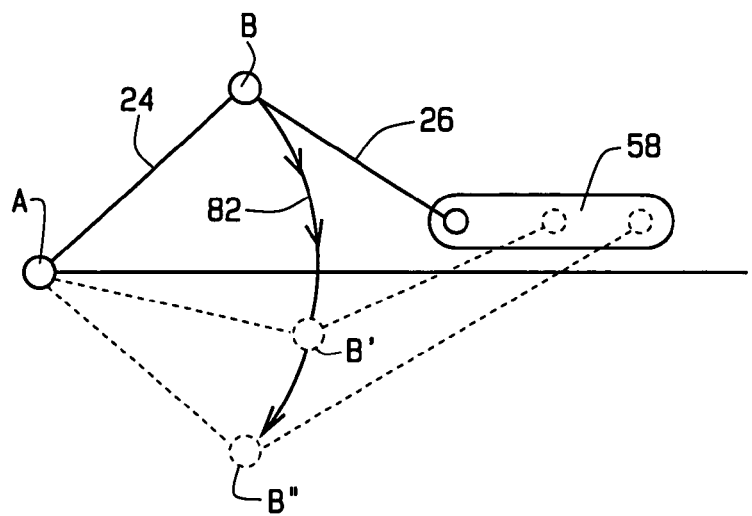
FIG. 8 is a graphic view showing the motion of operation of an embodiment of the present invention.

FIG. 8 is a graphic diagram showing a preferred arcuate movement of micokeratome 10 relative to suction ring 34. Pivot point A represents post 28 and letter B represents the main body of microkeratome 10 including motor 12 and letter C represents post 26 moving within slot 58. When motor 12 causes arm 24 to move relative to arm 26, microkeratome 10 pivots at point A and moves arm C within slot 58 as shown, causing B to move along arcuate path 82. Position B' corresponds to position C' with the following position B" corresponding to the final position C". So that the preferred arcuate movement within slot 58 moves post 26 from position C to C' at the far end of slot 58 and then back to C" towards the middle of slot 58. By providing for such a movement a more compact and stable bar-link design may be achieved rather than having post C move along a straight line continually away from pivot point A from beginning to end. As those skilled in the art will appreciate, the drive B does not need to include the preferred motor. The drive could be powered manually by a surgeon pivoting the microkeratome in his fingers. A motor to oscillate a blade assembly would still be desired. Also, two motors—one for oscillation and one for translation—could be employed.

Figure 9:
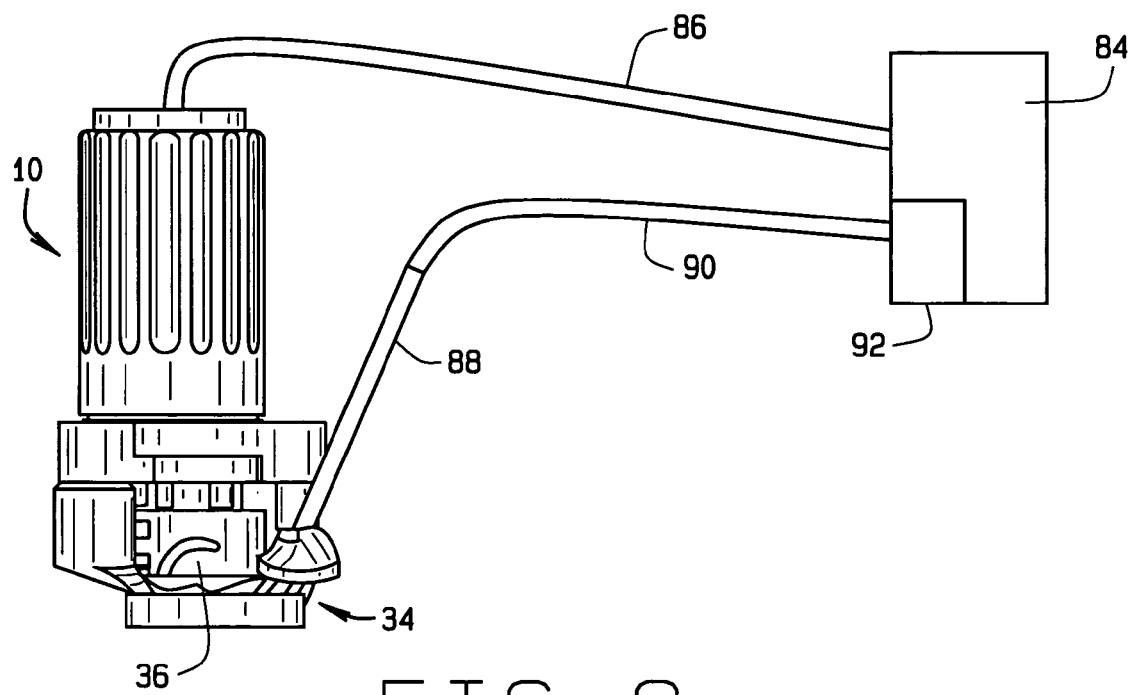
FIG. 9 shows a microkeratome in accordance with the present invention connected to a control box.

FIG. 9 shows a microkeratome 10 including a controller 84 connected to drive 20 including motor 12 via cable 86 and also connected to the fixation ring 34 via suction post 88 and tubing 90 for controlling movement of the cutting-head 36 and the attachment of the ring 34 to the patient's eye. Controller 84 also preferably includes a vacuum or suction source 92.

Controller 84 may also cooperate with a translation stop formed by pin 30 and slot 50 internal to the drive 20 to allow an adjustable hinge-width and an electronic translation stop. This may be achieved by having opto-couplers associated with slot 50 and pin 30 to measure the movement of pin 30 within slot 50 or mechanical sensors could also be used and controller 84 could be enabled to set a particular translation distance or hinge-width that may be desired by a surgeon. In all other respects controller 84 and microkeratome 10 preferably operate as described in the above referenced Hellenkamp patents. While the use of suction is highly preferred to affix ring 34 to an eye, other means are possible such as the use of cleats or adhesive.

Figure 10:
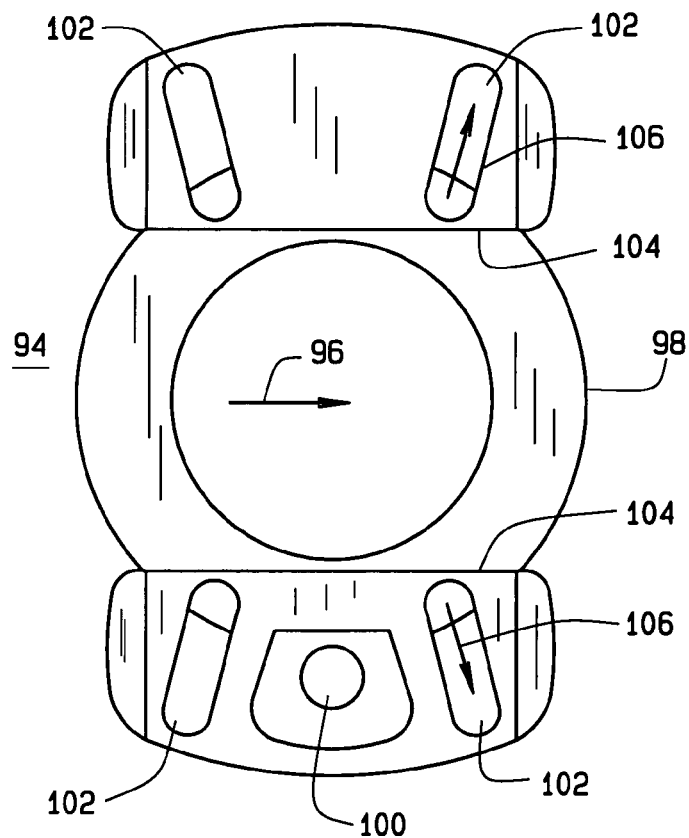
FIG. 10 is top view of a suction ring in accordance with an alternate embodiment of the present invention.

FIG. 10 shows an alternate embodiment of a fixation ring 94 for causing a cutting-head to move in a straight path across fixation ring 94 as indicated by arrow 96. Fixation ring 94 has an annular ring 98 similar to ring 64 and a passage 100 similar to passage 72 for allowing suction to affix ring 98 to a patient's eye. In addition, the slider-crank mechanism includes at least two slots 102 formed on the fixation ring 98 though preferably the four slots shown are formed on fixation ring 98. Suction ring 94 also preferably includes a pair of rails 104 for guiding the cutting-head along a path defined by the rails 104 across the fixation ring 94. In use, posts 26 and 28 will move within slots 102 along a path defined by arrows 106. As posts 26 and 28 move away from the center of fixation ring 94, cutting-head 36 moves along the path defined by arrow 96 as guided by rails 104. Rails 104 are similar to the slots 70, except that rails 104 forms a straight path across ring 98. Rails 104 receive flanges 68 of cutting-head 36. In this way, structure is attached to an upper-surface of the annular ring 98 and defines at least first and second slots 102 on opposing sides of the annular ring 98 to allow the same microkeratome assembly described above to travel in a straight line across suction ring 94, as opposed to the accurate movement described with respect to fixation ring 34. The use of different suction rings to achieve different translation paths across a patient's eye, greatly adds to the versatility, flexibility, and potential usefulness to a surgeon who may prefer different translation paths for different patients.

Figure 11:
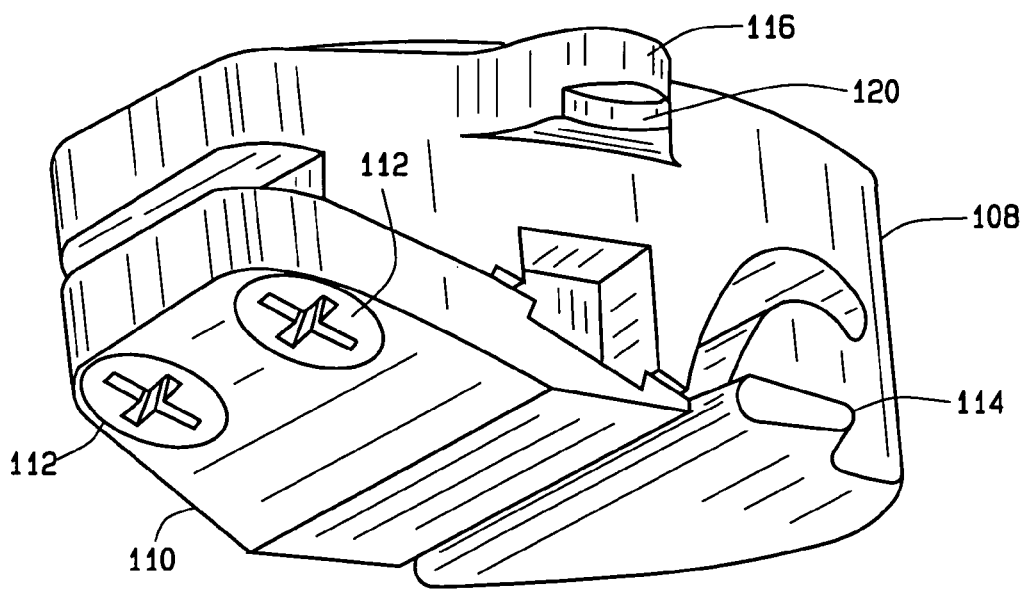
FIG. 11 is another alternate embodiment of a cutting-head assembly in accordance with the present invention.

FIG. 11 shows an alternate embodiment of a cutting-head 108. Cutting-head 108 is similar in construction to cutting-head 36 described above in that it holds a cutting blade assembly (not shown) preferably using door 110 and screws 112 and has flanges 114 which are essentially identical to flanges 68. Cutting-head 108 differs from cutting-head 36 in that no arms 78 exists and knobs 116 mate with the structure defining a pivot hole onto an alternate embodiment fixation ring 118, shown in FIG. 12.

Figure 12:
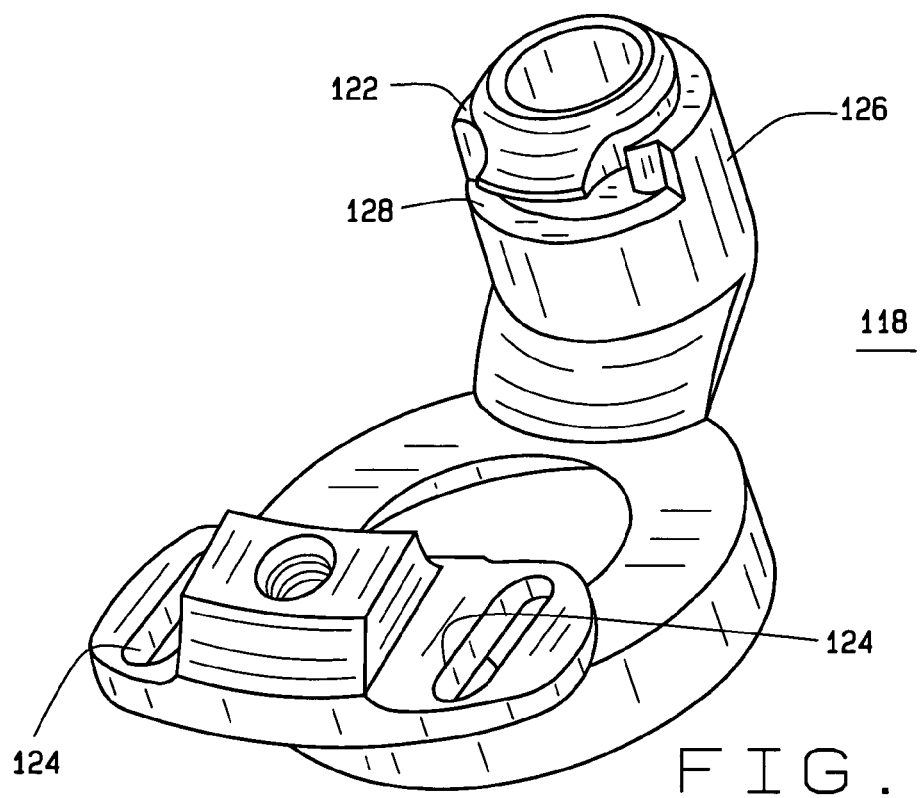
FIG. 12 is an alternate embodiment of a suction ring in accordance with the present invention and for use with the cutting-head assembly of FIG. 11.

During assembly of the microkeratome using cutting-head 108, knob 116 and in particular, the flange defined at 120 rides along an indentation formed at 122 of FIG. 12, which acts substantially the same way as elevation dowel pin 56 and arm posts 26 or 28, to hold the microkeratome assembly above the slots 124 until the arm posts are above slots 124 and ready to slide within the slots 124. The knob 116 then rotates about the pivot structure 126 within groove 128 during movement of the cutting-head assembly 108 across the fixation ring 118. Another difference between fixation ring 118 and fixation ring 34 is that no flanges are associated with the slots 124 because the arm posts of the alternative embodiment associated with FIGS. 11 and 12 do not include the slots 27. Therefore, attachment of a microkeratome to ring 118 during surgery relies on knob 116 mating with slot or groove 128 and flanges 114 mating with slot or groove 130, seen in FIG. 13, which is similar to slot 70 described above; in this way the microkeratome is maintained in a level position relative to ring 118 and attached to ring 118 to provide a smooth pivoting motion of the microkeratome across ring 118. It will be appreciated that knob 116 and slot 128 cooperate to perform essentially the same function as indents 80 on arms 78, as a cutting-head locator.

Figure 13:
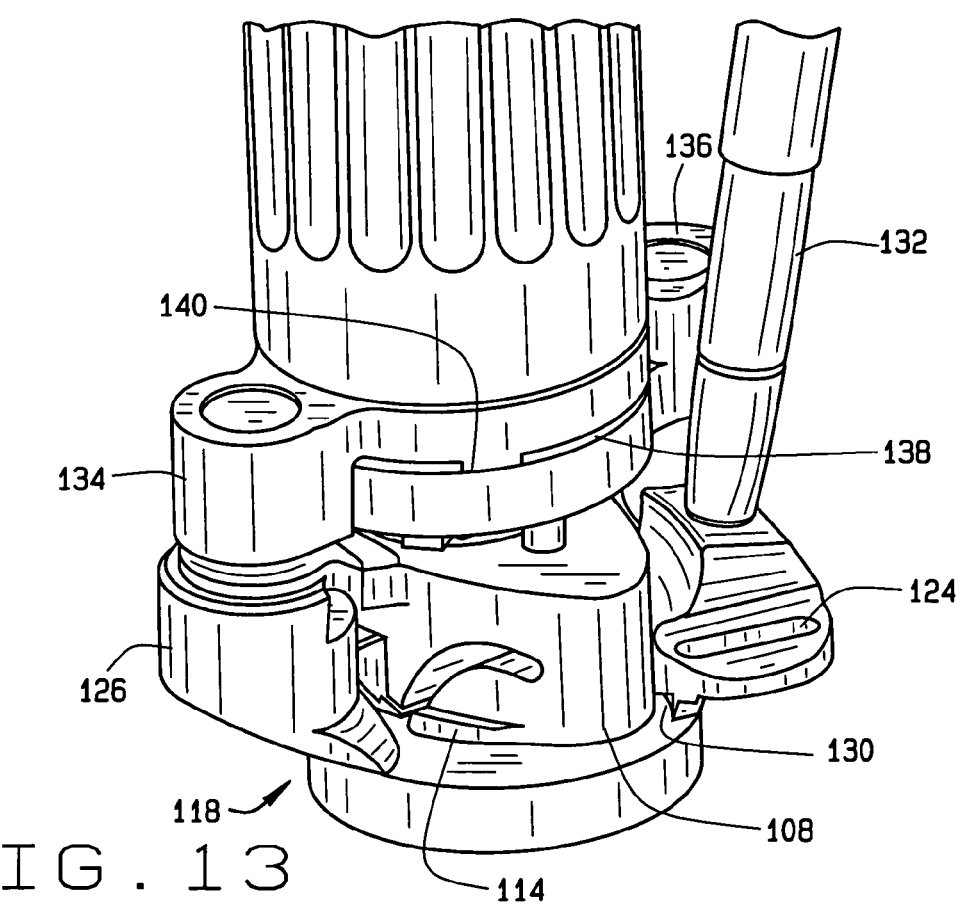
FIG. 13 is a partial perspective view of an alternate embodiment of the present invention.
Figure 14:
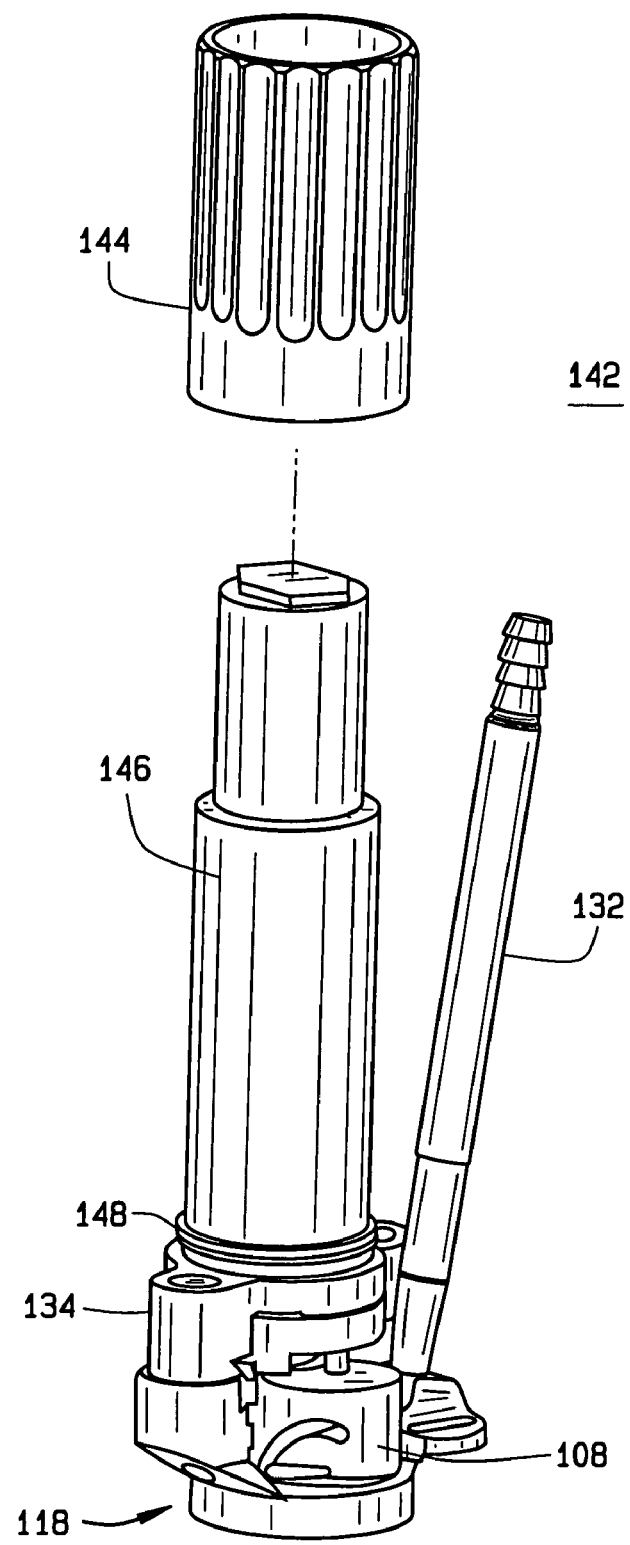
FIG. 14 is a partial exploded perspective view of an alternate embodiment of the present invention.

FIG. 13 shows a partial perspective view of an alternate embodiment of the microkeratome incorporating the cutting-head 108 and fixation ring 118 including a suction post 132. It is noted that drive arms 134 and 136 are generally separated a distance shown at 138 by the spurs 140 formed in drive arm 134. This spacing 138, which is preferably about 0.5 mm wide, allows for easier cleaning and autoclaving of the microkeratome drive assembly. The spurs 140 also stiffen up the coupling of arms 134 and 136 by assuring that spurs 140 always ride on the high portions of arm 136. The alternate embodiment microkeratome 142 using the cutting-head assembly and fixation rings of FIGS. 11-13 also preferably includes an outer sleeve 144 for attaching the motor 146 to the drive mechanism and specifically drive arm 134 via threads 148 as shown.

We claim:

1. A microkeratome for use in ophthalmic surgery comprising:
    a slider-crank mechanism;
    a cutting-head connected to the slider-crank mechanism;
    a fixation ring coupled to the slider-crank mechanism; and
    wherein the slider-crank mechanism moves the cutting-head at least partially across the fixation ring.

2. The microkeratome of claim 1 further including a controller connected to the slider-crank mechanism and fixation ring to control the movement of the cutting-head and the attachment of the ring to the patient's eye.

3. The microkeratome of claim 1, wherein the connection of the cutting-head to the slider-crank mechanism includes a snap-on connector requiring less than 360° of rotation of the cutting-head relative to the slider-crank mechanism.

4. The microkeratome of claim 1, wherein the slider-crank mechanism includes two (2) drive arms wherein each arm includes a link pin, each link pin including a slot such that one of the link pins mates with an elevation pin and the other pin mates with a flange of the fixation ring.

5. The microkeratome of claim 4, wherein the elevation pin of the fixation ring acts to hold the other link pin above a slot of the fixation ring to improve the ease of assembly of the slider-crank mechanism onto the fixation ring.

6. The microkeratome of claim 4 wherein each arm includes a link pin, such that the link pins mate with structure formed on the fixation ring for guiding the slider-crank mechanism at least partially across the fixation ring.

7. The microkeratome of claim 6 wherein a pivot hole of the fixation ring includes an indentation for mating with a knob of the cutting-head for holding one of the link pins above a slot of the fixation ring.

8. The microkeratome of claim 1, wherein the slider-crank mechanism includes a left/right selector that is alternately moveable between a start position of the slider-crank mechanism for a patient's left eye and a start position for a patient's right eye.

9. The microkeratome of claim 1 further including a cutting-head locator for angularly positioning an axis of rotation of cutting-head.

10. The microkeratome of claim 9, wherein the cutting-head locator includes indents on opposite sides of the cutting-head for providing location for both left and right eyes of a patient.

11. The microkeratome of claim 9, wherein the cutting-head locator includes resilient spring-like arms.

12. The microkeratome of claim 1, wherein the fixation ring includes structure extending beyond a bottom-most part of an annular ring and raised above the bottom-most part of the annular ring for allowing the microkeratome to be rotated about a patient's eye without interference from the patient's nose, eyebrow, or cheek.

13. The microkeratome of claim 1, wherein the slider-crank mechanism includes a pivot hole and a slot formed on the fixation ring.

14. The microkeratome of claim 13, wherein the pivot hole and the slot are generally on opposing sides of the ring.

15. The microkeratome of claim 13, wherein the pivot hole and the slot cause the cutting head to move in an arcuate path across the fixation ring.

16. The microkeratome of claim 13, wherein the pivot hole and the slot cause the cutting head to move in a linear path across the fixation ring.

17. The microkeratome of claim 13, wherein a length of the slot determines the length of translation of the slider-crank mechanism across the fixation ring.

18. The microkeratome of claim 1 wherein the slider-crank mechanism includes at least two slots formed on the fixation ring and a pair of rails for causing the cutting-head to move along a path defined by the rails across the fixation ring.

19. The microkeratome of claim 1 further including a translation stop internal to the slider-crank mechanism for allowing adjustable hinge-width.

20. The microkeratome of claim 1 further including a motor for automatically driving the cutting head at least partially across the fixation ring.

21. The microkeratome of claim 1 further including a motor for oscillating a blade assembly within the cutting head.

22. The microkeratome of claim 1 further including a first motor for automatically driving the cutting head assembly and a second motor for oscillating a blade assembly within the cutting head assembly.

23. A microkeratome for use in ophthalmic surgery comprising:
    a slider-crank mechanism including a motor;
    a cutting-head connected to the slider-crank mechanism;
    a cutting blade assembly held within the cutting head;
    a fixation ring coupled to the slider-crank mechanism; and
    wherein the motor causes the slider-crank mechanism to move the cutting head assembly at least partially across the fixation ring and wherein the motor causes the cutting blade assembly to oscillate as the cutting head assembly translates across the fixation ring so that a flap of corneal tissue is formed on the eye.

24. The microkeratome of claim 23 further including a controller connected to the slider-crank mechanism and fixation to control the movement of the cutting-head and the attachment of the ring to the patient's eye.

25. The microkeratome of claim 23, wherein the connection of the cutting-head to the slider-crank mechanism includes a snap-on connector requiring less than 360° of rotation of the cutting-head relative to the slider-crank mechanism.

26. The microkeratome of claim 23, wherein the slider-crank mechanism includes a left/right selector that is alternately moveable between a start position of the slider-crank mechanism for a patient's left eye and a start position for a patient's right eye.

27. The microkeratome of claim 23, wherein the slider-crank mechanism includes structure forming a pivot hole and a slot on the fixation ring for causing the cutting-head to move in an accurate path across the fixation ring.

28. The microkeratome of claim 23, wherein the slider-crank mechanism includes at least two slots formed on the fixation ring and a pair of rails for causing the cutting-head to move along a path defined by the rails across the fixation ring.

29. The microkeratome of claim 23 further including a translation stop internal to the slider-crank mechanism for allowing adjustable hinge-width and an electronic translation stop.

* * * * *